United States Patent
Pyzyna et al.

(10) Patent No.: US 10,168,299 B2
(45) Date of Patent: Jan. 1, 2019

(54) REPRODUCIBLE AND MANUFACTURABLE NANOGAPS FOR EMBEDDED TRANSVERSE ELECTRODE PAIRS IN NANOCHANNELS

(71) Applicant: INTERNATIONAL BUSINESS MACHINES CORPORATION, Armonk, NY (US)

(72) Inventors: Adam M. Pyzyna, Cortlandt Manor, NY (US); Joshua T. Smith, Croton on Hudson, NY (US); Benjamin H. Wunsch, Mt. Kisco, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 231 days.

(21) Appl. No.: 15/211,413

(22) Filed: Jul. 15, 2016

(65) Prior Publication Data
US 2018/0017524 A1    Jan. 18, 2018

(51) Int. Cl.
*G01N 27/447* (2006.01)
*H01L 21/311* (2006.01)
(Continued)

(52) U.S. Cl.
CPC .... *G01N 27/44791* (2013.01); *B01L 3/50273* (2013.01); *B01L 3/502707* (2013.01);
(Continued)

(58) Field of Classification Search
CPC ............ G01N 27/3278; G01N 27/447; G01N 27/44791; H01L 21/31116; H01L 21/31053; B01L 2200/10; B01L 2200/12; B01L 2300/0896
See application file for complete search history.

(56) References Cited

U.S. PATENT DOCUMENTS

| | | | |
|---|---|---|---|
| 8,039,368 B2 | 10/2011 | Drndic et al. | |
| 8,710,444 B2 | 4/2014 | Kim et al. | |
| (Continued) | | | |

FOREIGN PATENT DOCUMENTS

| | | |
|---|---|---|
| CN | 100559272 C | 11/2009 |
| CN | 102393453 B | 9/2013 |
| WO | 2015167019 A1 | 11/2015 |

OTHER PUBLICATIONS

List of IBM Patents or Patent Applications Treated as Related dated Aug. 30, 2016, 2 pages.
(Continued)

*Primary Examiner* — Bethany L Martin
(74) *Attorney, Agent, or Firm* — Tutunjian & Bitetto, P.C.; Vazken Alexanian

(57) ABSTRACT

A method for forming a nanogap includes forming a knock-off feature on a dielectric layer and forming a trench in the dielectric layer on opposite sides of the knockoff feature. A noble metal is deposited in the trenches and over the knockoff feature. A top surface is polished to level the noble metal in the trenches with a top of the dielectric layer to form electrodes in the trenches and to remove the noble metal from the knockoff feature. A nanochannel is etched into the dielectric layer such that the knockoff feature is positioned within the nanochannel. The knockoff feature is removed to form a nanogap between the electrodes.

17 Claims, 4 Drawing Sheets

(51) Int. Cl.
  *H01L 21/321* (2006.01)
  *H01L 21/3105* (2006.01)
  *H01L 21/02* (2006.01)
  *H01L 21/3205* (2006.01)
  *B01L 3/00* (2006.01)

(52) U.S. Cl.
  CPC .. *H01L 21/02134* (2013.01); *H01L 21/31053* (2013.01); *H01L 21/31116* (2013.01); *H01L 21/32051* (2013.01); *H01L 21/32115* (2013.01); *B01L 2200/10* (2013.01); *B01L 2300/0645* (2013.01); *B01L 2300/0887* (2013.01); *B01L 2400/0421* (2013.01)

(56) References Cited

U.S. PATENT DOCUMENTS

| | | | |
|---|---|---|---|
| 8,747,604 B2 | 6/2014 | Gosnet-Haghiri et al. | |
| 8,882,980 B2 | 11/2014 | Ling et al. | |
| 8,918,152 B2 | 12/2014 | Strachan et al. | |
| 8,926,813 B2 | 1/2015 | Oliver | |
| 8,940,663 B2 | 1/2015 | Iqbal et al. | |
| 9,097,698 B2 | 8/2015 | Astier et al. | |
| 9,128,078 B2 | 9/2015 | Astier et al. | |
| 2002/0079552 A1* | 6/2002 | Koike | H01L 23/5258 257/529 |
| 2003/0040172 A1* | 2/2003 | Brennan | H01L 21/31144 438/622 |
| 2013/0265031 A1 | 10/2013 | Shim et al. | |

OTHER PUBLICATIONS

Liang, X. et al., "Nanogap Detector Inside Nanofluidic Channel for Fast Real-Time Label-Free DNA Analysis" Nano Letters (Feb. 2008) pp. 1472-1476, vol. 8, No. 5.

Chen, X. et al., "Electrical nanogap devices for biosensing" Materials Today (Nov. 2010) pp. 28-41, vol. 13, No. 11.

List of IBM Patents or Patent Applications Treated as Related dated Jul. 15, 2016, 2 pages.

* cited by examiner

REPRODUCIBLE AND MANUFACTURABLE NANOGAPS FOR EMBEDDED TRANSVERSE ELECTRODE PAIRS IN NANOCHANNELS

BACKGROUND

Technical Field

The present invention generally relates to nanochannel devices and methods for making the same, and more particularly to methods and devices with reproducible nanogaps formed between electrodes within the nanochannel.

Description of the Related Art

On-chip electrodes can be incorporated into lab-on-a-chip (LOC) or micro total analysis systems (µTAS) to perform several functions, such as sorting of charged biological material, electrokinetic driving of the same to induce flow in a specific direction, or for sensing biomolecules by transducing events into electrical signals when electrodes are configured in a nanogap arrangement. In the latter case, the electrode tips need to be in close proximity to detect nanoscale (<100 nm) biocolloids of broad interest to biotechnology companies and academics alike, such as DNA, exosomes, viruses, protein aggregates, etc.

The use of noble metals as the electrode material is desirable to avoid irreversible modification processes, such as oxidation, of the electrodes as the electrodes interface with the microfluidic environment; however, these materials are extremely difficult to pattern, particularly at nanoscale dimensions.

Control over nanogap dimensions has employed He ion beams to cut noble metal nanowires into a set of nanogap electrodes and even within nanochannels. However, use of a He beam to cut precision gaps requires labor intensive manual operation to align and cut the gaps (i.e., relatively low throughput), and the noble metal splatters locally during the cut redistributing metal around the incision that may have deleterious effects on the surface of the channel close to the proximity of the gap. This ultimately impedes or completely restricts fluid flow through the detection device.

Additionally, He beam cutting on $SiO_2$ over silicon causes swelling of the silicon, which further complicates analysis. Besides angled deposition techniques and He beam cutting to form a nanogap in metal electrodes, self-aligned sacrificial metal, electromigration, or dry/wet etching approaches have also been employed to form a gap, but all of these methods result in low process control, large nanogap variation, and/or low yield.

SUMMARY

In accordance with an embodiment of the present principles, a method for forming a nanogap includes forming a knockoff feature on a dielectric layer and forming a trench in the dielectric layer on opposite sides of the knockoff feature. A noble metal is deposited in the trenches and over the knockoff feature. A top surface is polished to remove the noble metal from regions outside the trenches including the knockoff feature, leaving the noble metal only in the trenches with the noble metal surface being coplanar with a top of the dielectric layer to form electrodes in the trenches. A nanochannel is etched into the dielectric layer such that the knockoff feature is positioned within the nanochannel. The knockoff feature is removed during the polish with the subsequent nanochannel etch to form a nanogap between the electrodes.

Another method for forming a nanogap includes forming a hydrogen silsesquioxane (HSQ) knockoff feature on a dielectric layer; forming a trench in the dielectric layer on opposite sides of the knockoff feature, the trenches including electrode and nanoelectrode shapes; depositing a noble metal in the trenches and over the knockoff feature; polishing a top surface to remove the noble metal in field regions and the knockoff feature, leaving the noble metal in the trenches level with a top of the dielectric layer to form embedded electrodes and nanoelectrodes in the trenches; etching a nanochannel in the dielectric layer such that the knockoff feature is positioned within the nanochannel; and removing the knockoff feature to form a nanogap between the nanoelectrodes.

A nanochannel device includes a substrate, a dielectric layer formed on the substrate and a nanochannel etched into the dielectric layer. A first noble metal electrode includes a first nanoelectrode extending into the nanochannel, and a second noble metal electrode includes a second nanoelectrode extending into the nanochannel. The first noble metal electrode and the second noble metal electrode are monolithically and independently formed on either side of a nanogap disposed between the first nanoelectrode and second nanoelectrode.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The disclosure will provide details in the following description of preferred embodiments with reference to the following figures wherein.

DETAILED DESCRIPTION

Figure 1:
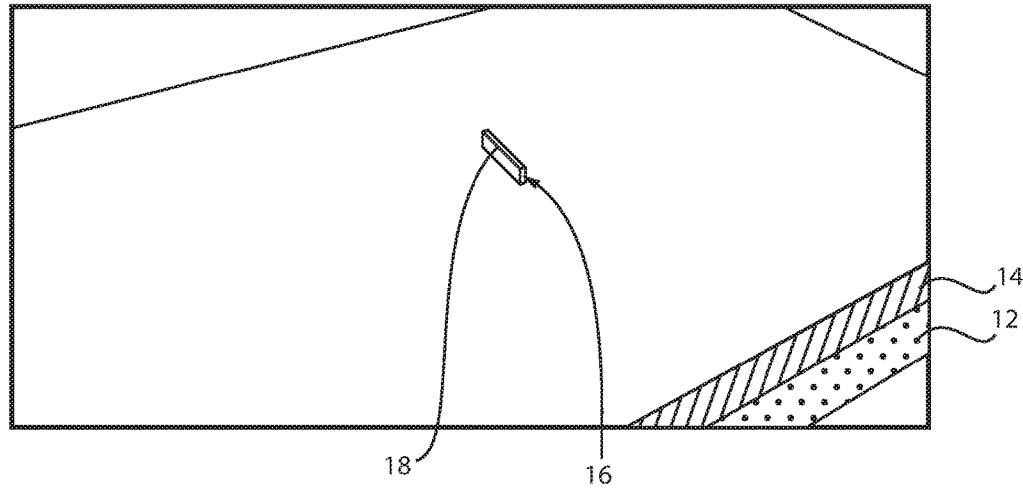
FIG. 1 is a perspective cross-sectional view showing a knockoff feature formed on a dielectric layer in accordance with the present principles.

In accordance with the present principles, devices and methods for manufacturing a nanogap are provided. The methods include forming a dielectric (e.g., oxide) on a wafer (e.g., silicon) and defining a sacrificial knockoff layer (e.g., formed from hydrogen silsesquioxane (HSQ)) in a location where the nanogap is to be formed. A trench is etched into the dielectric using a patterned resist and a reactive-ion etch (RIE). A noble metal (e.g., palladium, platinum, gold, etc.) is deposited on the same patterned resist to fill the trench, forming two separate nanowire electrodes straddling the knockoff layer. A polish is used to release unwanted metal including metal atop the HSQ line and resist. A nanochannel is etched through the polished HSQ and leaves a nanogap between portions of the noble metal (electrodes).

A robust and high-yield means of fabricating controlled nanogaps (down to, e.g., 7 nm) within embedded noble metal nanowire electrodes is provided. A configuration of pairs of transverse electrodes straddling a nanochannel results. This arrangement is difficult to achieve in practice for noble metals, but is needed for electrical detection and sensing of biomolecules and other materials for lab-on-a-chip (LOC) applications. The electrodes can be embedded in a dielectric (e.g., an oxide) to provide both electrical isolation and a sealable platform for microfluidic detection devices. In one embodiment, the noble metal is embedded such that a surface of the metal is coplanar with an oxide surface. A polish may be a water-based polish using only mechanical forces and a water medium to release the resist and unwanted metal atop the resist surface from the dielectric layer beneath. Different from chemical-mechanical polishing (CMP), there is no requirement for a corrosive chemical slurry.

The present principles fabricate, down to sub-10 nm, nanogaps in noble metal nanowire electrodes transverse to a nanochannel for detection of biomolecules, including polymers such as tagged or untagged DNA and RNA as well as a variety of nanoparticles, including exosomes, viruses, proteins, quantum dots, etc. Nanogaps are formed by implementing a sacrificial HSQ knockoff layer defined prior to electrode trench formation and subsequent metal deposition processes. Used in conjunction with a water-based mechanical polishing procedure, these methods provide a way of fabricating, e.g., a minimum of over 7,600 such nanogaps in less than an hour over a 200 mm wafer surface using standard electron beam lithography. These gaps have both exceptionally high yield and a narrow nanogap width variation (e.g., less than a few nanometers).

Creating electrodes that can interface with microfluidics to sense material contained within the fluid is challenging. Standard methods for forming a metal electrode include some form of lithography to form the desired pattern in a sacrificial resist material followed by a metallization and liftoff processes, or a subtractive patterning technique in which metal is blanket coated over a substrate surface followed by a resist patterning and etch process flow. These techniques are not sufficient to create thin metal electrodes embedded in an oxide with boundaries well aligned to the oxide edges. Erosion of the resist sidewall from the reactive-ion etch (RIE) used to create the trenches within the oxide leads to coverage of the resist with the noble metal that is subsequently deposited to fill the trenches to create the electrodes, leading to low-yield liftoff problems.

To make a manfacturable nanogap, sacrificial HSQ lines are defined prior to trench definition and metal deposition using electron beam (ebeam) lithography. After metal deposition, the HSQ lines (with metal on top, e.g., HSQ 2% material and HSQ 6% material line widths) act as a knockoff layer that is sheared off during a polish process. The HSQ is left uncured to ensure easy removal. Any HSQ residual is etched during the nanochannel etch process, which etches uncured HSQ much faster than $SiO_2$. This ensures etch depth uniformity of the nanochannel.

In experiments, gap uniformity for various line widths defined by ebeam lithography is provided. Further, gap yield was 100% for over 80 randomly located nanogaps inspected by scanning electron microscopy (SEM). In one embodiment, gap sizes down to 7 nm were reproducibly shown for HSQ 2% lines designed at a width of 20 nm with a writing resolution of 5 nm.

It is to be understood that the present invention will be described in terms of a given illustrative architecture; however, other architectures, structures, substrate materials and process features and steps may be varied within the scope of the present invention.

It will also be understood that when an element such as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The present embodiments may include a design for an integrated circuit chip, which may be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer may transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

It should also be understood that material compounds will be described in terms of listed elements, e.g., SiGe. These compounds include different proportions of the elements within the compound, e.g., SiGe includes $Si_xGe_{1-x}$ where x is less than or equal to 1, etc. In addition, other elements may be included in the compound and still function in accordance with the present principles. The compounds with additional elements will be referred to herein as alloys.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, may be used herein for ease of description to describe one element's or feature's relationship to another element(s) or feature(s) as illustrated in the FIGS. It will be understood that the spatially relative terms are intended to encompass different orientations of the device in use or operation in addition to the orientation depicted in the FIGS. For example, if the device in the FIGS. is turned over, elements described as "below" or "beneath" other elements or features would then be oriented "above" the other elements or features. Thus, the term "below" can encompass both an orientation of above and below. The device may be otherwise oriented (rotated 90 degrees or at other orientations), and the spatially relative descriptors used herein may be interpreted accordingly. In addition, it will also be understood that when a layer is referred to as being "between" two layers, it can be the only layer between the two layers, or one or more intervening layers may also be present.

It will be understood that, although the terms first, second, etc. may be used herein to describe various elements, these elements should not be limited by these terms. These terms are only used to distinguish one element from another element. Thus, a first element discussed below could be termed a second element without departing from the scope of the present concept.

Referring now to the drawings in which like numerals represent the same or similar elements and initially to FIG. 1, a substrate 12 includes a dielectric layer 14 formed thereon. The substrate 12 may include any suitable substrate material or materials. For example, the substrate may include a semiconductor material, a ceramic, glass, quartz, etc. In one embodiment, the substrate 12 includes a silicon based semiconductor material, e.g., Si, SiGe, SiC, etc. and the dielectric layer 14 may include a silicon oxide. The dielectric layer 14 may be grown, transferred or deposited on the substrate 12.

A nanogap location is defined by forming a knockoff layer 16 and patterning the knockoff layer 16 to form a knockoff feature 18. The knockoff layer 16 may be spun onto the surface of the dielectric layer 14. The knockoff layer 16 may include a high resolution resist, such as hydrogen silsesquioxane (HSQ) or other resist material that can be defined using an electron beam (ebeam) or the like. In one embodiment, the knockoff feature 18 is written in the knockoff layer 16 using ebeam lithography to define a narrow line for the knockoff feature 18. In one useful embodiment, the HSQ, a high resolution negative ebeam resist, is reacted using the ebeam, and the remainder of the resist is removed by a developer leaving only the knockoff feature 18 on the dielectric layer 14. The knockoff feature 18 will serve as a release layer to remove metal deposited in the gap region in subsequent steps.

Figure 2:
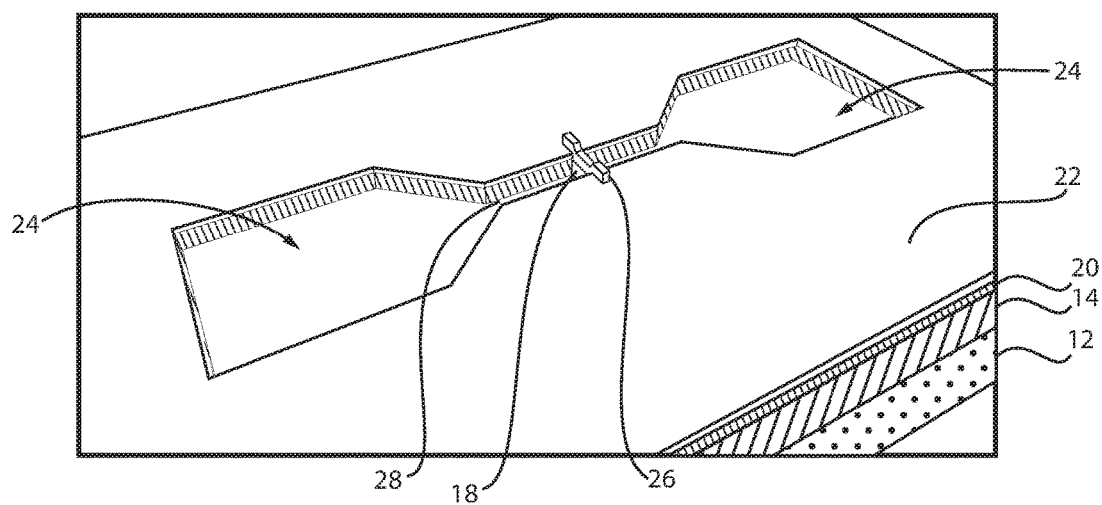
FIG. 2 is a perspective cross-sectional view showing trenches etched on opposite sides of the knockoff feature and a noble metal deposited in accordance with the present principles.

Referring to FIG. 2, a resist 20 is deposited or spun onto a surface of the dielectric layer 14. The resist 20 buries the knockoff feature 18 therein. The resist 20 is exposed to light, etc. to define a pattern for electrode formation. The resist 20 is exposed to a pattern of radiation and then developed utilizing a resist developer. Once the patterning of the resist is completed, the sections of the dielectric layer that are covered by the resist 20 are protected while the exposed regions are partially removed, e.g., removed up to a well-defined depth, using a selective etching process that removes the unprotected regions of the dielectric layer 14 in the form of a well or trench 24 that defines the desired geometry of the electrodes. The etch process may include a reactive ion etch (RIE). The trench 24 is etched into a dielectric layer 14 to provide for electrical isolation.

The RIE does not remove the knockoff feature 18, which remains on the dielectric layer 14 and within the resist 20, however, the knockoff feature 18 may be slightly eroded during the RIE process making it slightly thinner than the width defined by ebeam lithography. The knockoff feature 18 remains in a gap region 28 between the electrode shapes in the trench 24. The RIE forms anisotropic trench walls without undercutting of the resist 20.

Once the trench 24 is formed into the dielectric layer 20, a metal layer 22 is deposited, which covers the resist 20 outside the trench 24 (field regions) and the dielectric layer 14 in the trench 24. Prior to deposition of the metal layer 22, a thin adhesion layer (not shown) may be deposited, e.g., 0.2 nm-2 nm of Ti or Cr. The adhesion layer may be formed so that the noble metal of metal layer 22 will not delaminate.

The metal deposition process also covers the knockoff feature 18 with a metal portion 26 as well. The metal layer 22 is excluded from the area where the knockoff feature 18 is located in the gap region 28. The metal deposition process may include chemical vapor deposition (CVD), atomic layer deposition (ALD), sputtering, etc. In one embodiment, e-beam evaporation is employed to fill the trench 24 with a noble metal until the metal layer is coplanar with the surface of the dielectric layer 14. The noble metal 22 may include Pd, Pt, Au, etc.

The electrodes 30 are monolithically formed independently of each other since they are separated by the knockoff feature 18. The electrodes 30 are formed on either side of the nanogap formed between nanoelectrodes 32 as shown in FIG. 3.

Figure 3:
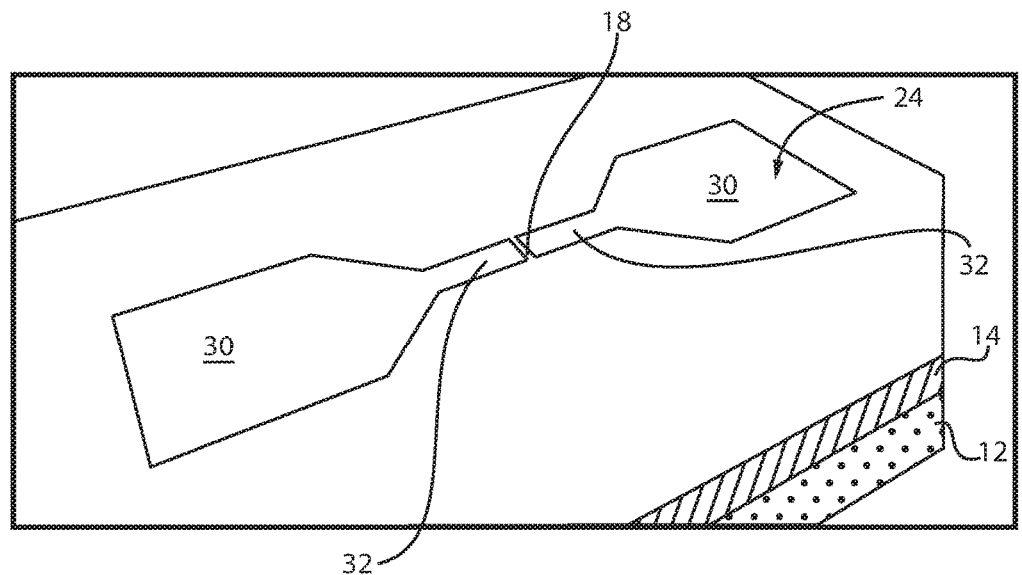
FIG. 3 is a perspective cross-sectional view showing the noble metal planarized with electrodes in the trenches on opposite sides of the knockoff feature and the noble metal being level with the dielectric layer in accordance with the present principles.

Referring to FIG. 3, a planarization process is employed to remove unwanted metal 22 and resist 20. In one embodiment, a water polish is employed. The water polish uses an appropriate down force to selectively and concurrently remove the resist 20 (which acts as a release layer), the knockoff feature 18 and unwanted metal 22 in the field regions while keeping electrodes 30 in the trenches intact. The polish process reduces fencing that can occur at the boundaries of deposited materials defined by traditional liftoff. Electrodes 30 and transverse nanoelectrodes 32 are formed from the metal layer 22 (e.g., by controlling the deposition rate and having a well-defined RIE etch process). The etch exposes the knockoff feature 18, which will be employed to form a nanogap.

In this way, the two electrodes 30 (and nanoelectrodes 32) are monolithically and independently formed on either side of the nanogap 38 disposed between the nanoelectrodes 32. Each electrode 30 is spaced apart from the other by the knockout feature 18.

Figure 4:
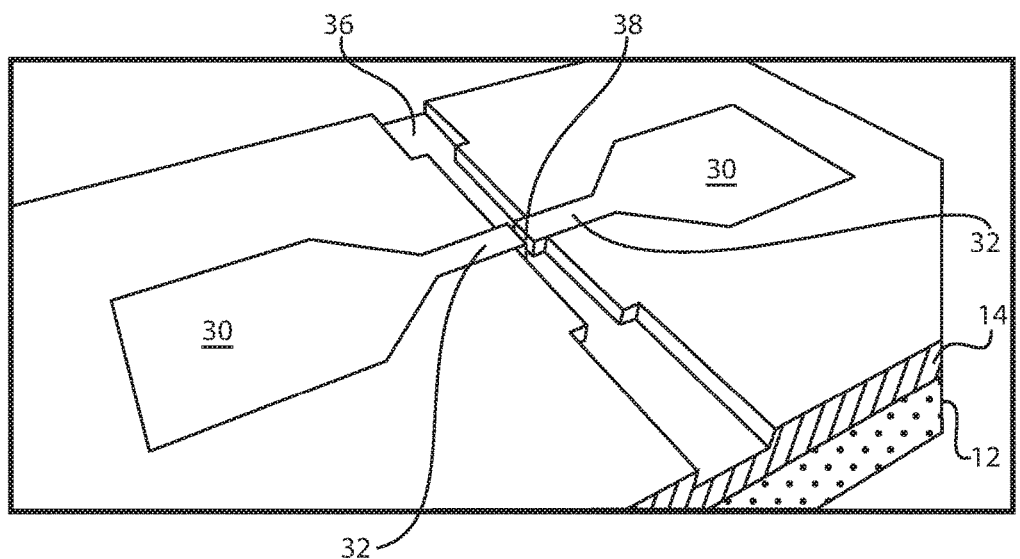
FIG. 4 is a perspective cross-sectional view showing a nanochannel formed in the dielectric layer and having a nanogap formed within the nanochannel in accordance with the present principles.

Referring to FIG. 4, lithography or other techniques are employed to further pattern the dielectric layer 14. A nanochannel 36 is formed in the dielectric layer 14. The nanochannel 36 coincides with the nanogap 38. The nanogap 38 is formed by removing the knockoff feature 18. The knockoff feature 18 may be removed in the etching/formation of the nanochannel 36 or may be removed by a separate etch process. A RIE etch may be employed that is channel aligned to the transverse nanoelectrodes 32 (nanowires).

In accordance with the present principles, a nanochannel 36 is formed having a nanogap 38 between two electrodes 30. The electrodes 30 are formed with a noble metal to prevent corrosion and degradation, and the nanogap 38 is formed reliably and accurately. In particularly useful embodiments, the nanogap is formed having a gap width or between about 2 nm and about 100 nm.

Figure 5:
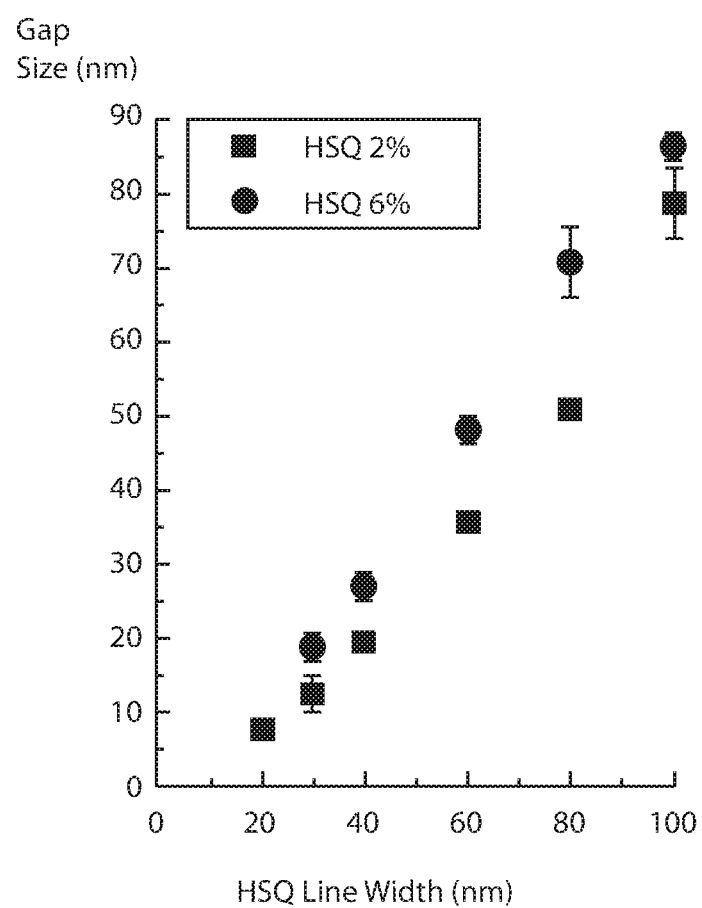
FIG. 5 is a plot of gap size (nm) versus knockoff feature line width (nm) for HSQ 2% and HSQ 6% in accordance with the present principles.

Referring to FIG. 5, a plot of gap size (nm) versus knockoff feature (HSQ) line width (nm) is illustratively shown. Electrode structures fabricated in accordance with the present principles were tested for nanogap (38) size versus knockout feature (18) design width to find a smallest possible gap dimension achievable. Arrays of knockout feature (18) linewidths of 5, 10, 20, 30, 40, 60, 80, and 100 nm were fabricated as shown and a 50 nm nanochannel was cut through the nanogaps, exposing the gap (e.g., for linewidths for HSQ 2% (gap=40 nm) and HSQ 6% (gap=120 nm)). HSQ 2% and HSQ 6% designate different dilutions of HSQ, namely, HSQ from 2% solution and HSQ from a 6% solution. In practice, other dilutions may be used as well, e.g., HSQ 4%, etc.

All of the gaps inspected (over 80 in this experiment) showed clear separation of the electrodes and a systematic increase in the size of the gap with increased line widths (or HSQ employed for the knockout feature 18). Data provided a clear linear correlation between the gap size (nanogap 38) and the starting line width of HSQ employed for the knockout feature 18. For all practical nanogap sizes (those relevant to DNA sensing and mapping) e.g., <40 nm, gap variation was at most 2 nm.

Figure 6:
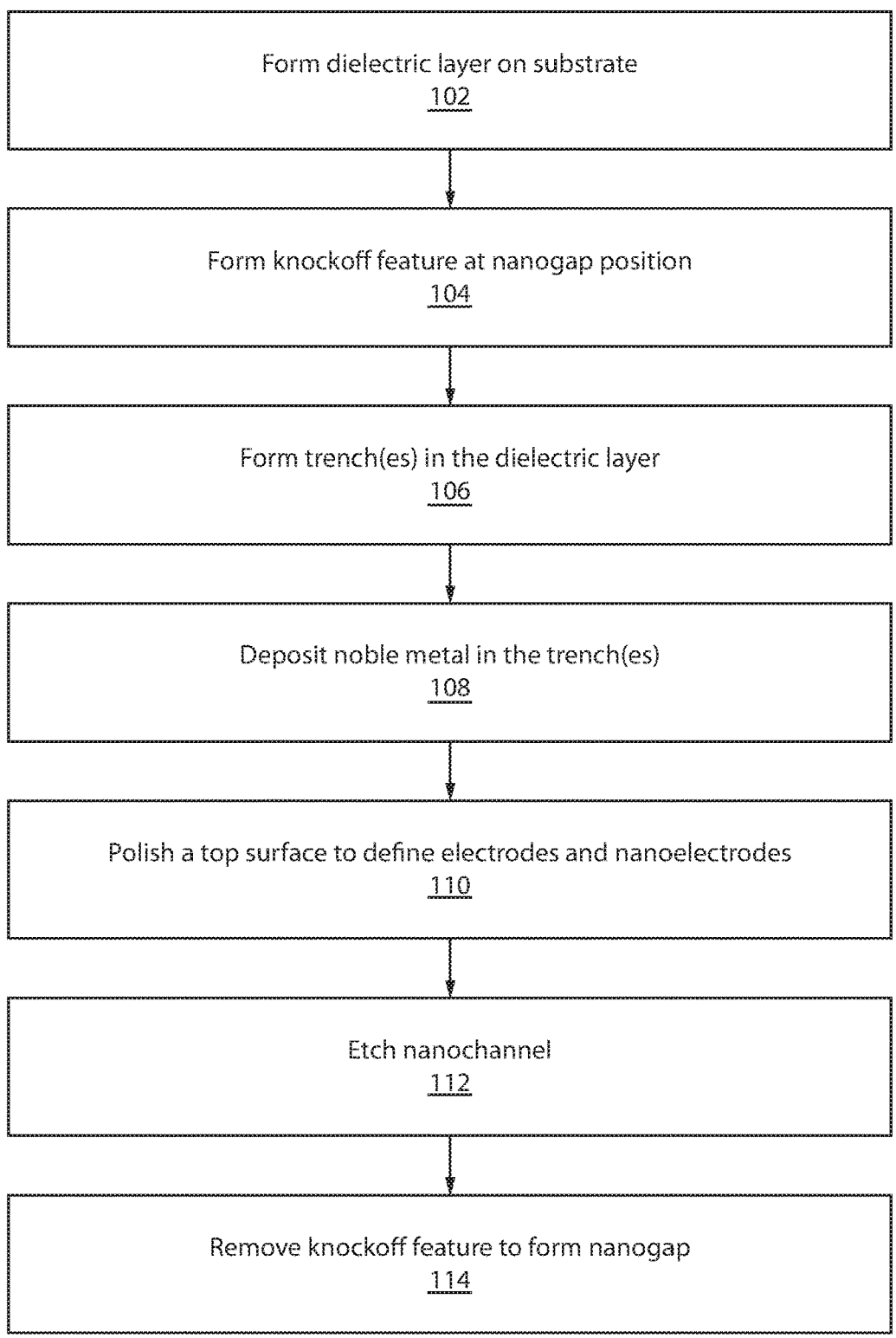
FIG. 6 is a block/flow diagram showing a method for forming a nanogap in accordance with the present principles.

Referring to FIG. 6, a method for forming a nanogap is shown in accordance with the present principles. In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In block 102, a dielectric layer is formed on a substrate. The dielectric layer may include a silicon oxide, although other dielectric materials may be employed. For example, the dielectric layer may include an oxide, nitride and oxynitride material.

In block 104, a knockoff feature may be formed on a dielectric layer. In one embodiment, a negative electron beam (ebeam) resist is deposited or spun onto the dielectric layer. A line or other elongated shape is exposed to an ebeam to create the knockout feature in the resist, defining the feature position of the nanogap. The resist is developed to remove all portions except the knockout feature. In one embodiment, the negative ebeam resist includes a HSQ material, which forms the knockoff feature on the dielectric layer.

In block 106, a trench or trenches are formed in the dielectric layer on opposite sides of the knockoff feature. The trench defines the shape of electrodes and nanoelectrodes (e.g., the part of the electrode that extends into the nanochannel in later steps). The trenches may be formed by depositing a resist layer and patterning the resist layer to open up electrode and nanoelectrode shapes adjacent to the nanogap. The trenches are etched in accordance with a resist pattern. The etch may include a RIE.

In block 108, a noble metal is deposited in the trenches and over the knockoff feature. An adhesion layer may precede the noble metal deposition. The noble metal may be deposited by electron bean evaporation. The noble metal may include a metal selected from the group consisting of Pd, Pt and Au. Other noble metals may also be employed.

In block 110, a top surface is polished to level the noble metal in the trenches with a top of the dielectric layer to form electrodes in the trenches and to remove the noble metal from the knockoff feature. The polishing may include a water polish.

In block 112, a nanochannel is etched in the dielectric layer such that the knockoff feature is positioned within the nanochannel. In block 114, the knockoff feature is removed to form a nanogap between the electrodes. The nanogap includes a width of between about 2 nm and about 20 nm, although dimensions up to 100 nm may be employed. The knockoff feature and the nanogap have a known dimensional relationship. In one embodiment, the known dimensional relationship is linear. The dimension of the knockoff features provides repeatable dimensions for the nanogap. The nanogap variation is less than about 2 nm from an intended nominal dimension.

Having described preferred embodiments reproducible and manufacturable nanogaps for embedded transverse electrode pairs in nanochannels (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for forming a nanogap, comprising:
   forming a knockoff feature on a dielectric layer;
   forming a trench in the dielectric layer on opposite sides of the knockoff feature;
   depositing a noble metal in the trenches and over the knockoff feature;
   polishing a top surface to remove the noble metal in field regions and the knockoff feature, leaving the noble metal in the trenches level with a top of the dielectric layer to form electrodes embedded in the trenches;
   etching a nanochannel in the dielectric layer such that the knockoff feature is positioned within the nanochannel; and
   removing the knockoff feature to form a nanogap between the electrodes and the nanogap lies within the nanochannel.

2. The method as recited in claim 1, wherein forming the knockoff feature includes:
   depositing a negative electron beam (ebeam) resist;
   exposing a line in the resist with an ebeam at a position of the nanogap to provide the knockout feature; and
   developing away the resist to leave the knockout feature.

3. The method as recited in claim 1, wherein forming the trench includes:
   depositing a resist layer;
   patterning the resist layer to open up electrode and nanoelectrode shapes adjacent to the nanogap; and
   etching the trenches in accordance with a resist pattern.

4. The method as recited in claim 1, wherein depositing the noble metal includes depositing the noble metal by electron beam evaporation.

5. The method as recited in claim 1, wherein depositing the noble metal includes depositing the noble metal selected from the group consisting of Pd, Pt and Au.

6. The method as recited in claim 1, wherein polishing the top surface includes water polishing.

7. The method as recited in claim 1, wherein the nanogap includes a width of between about 2 nm and about 50 nm.

8. The method as recited in claim 1, wherein fowling the knockoff feature on the dielectric layer includes forming a hydrogen silsesquioxane (HSQ) knockoff feature on the dielectric layer.

9. The method as recited in claim 1, wherein the knockoff feature and the nanogap have a known dimensional relationship.

10. A method for forming a nanogap, comprising:
    forming a hydrogen silsesquioxane (HSQ) knockoff feature on a dielectric layer;
    forming a trench in the dielectric layer on opposite sides of the knockoff feature, the trenches including electrode and nanoelectrode shapes;
    depositing a noble metal in the trenches and over the knockoff feature;
    polishing a top surface to remove the noble metal in field regions and the knockoff feature, leaving the noble metal in the trenches level with a top of the dielectric layer to form embedded electrodes and nanoelectrodes in the trenches;
    etching a nanochannel in the dielectric layer such that the knockoff feature is positioned within the nanochannel; and
    removing the knockoff feature to form a nanogap between the nanoelectrodes and the nanogap lies within the nanochannel.

11. The method as recited in claim 10, wherein forming the knockoff feature includes:
    depositing a negative electron beam (ebeam) resist including HSQ;
    exposing a line in the resist at a position of the nanogap to an ebeam to provide the knockout feature; and
    developing away the resist to leave the knockout feature.

12. The method as recited in claim 10, wherein forming the trench includes:
    depositing a resist layer;
    patterning the resist layer to open up the electrode and nanoelectrode shapes adjacent to the nanogap; and
    etching the trenches in accordance with a resist pattern.

13. The method as recited in claim 10, wherein depositing the noble metal includes depositing the noble metal by electron beam evaporation.

14. The method as recited in claim 10, wherein depositing the noble metal includes depositing the noble metal selected from the group consisting of Pd, Pt and Au.

15. The method as recited in claim 10, wherein polishing the top surface includes water polishing.

16. The method as recited in claim 10, wherein the nanogap includes a width of between about 2 nm and about 50 nm.

17. The method as recited in claim 10, wherein the knockoff feature and the nanogap have a known dimensional relationship.

* * * * *